United States Patent
Iino et al.

(10) Patent No.: US 11,592,440 B2
(45) Date of Patent: Feb. 28, 2023

(54) BIOPARTICLE MEASURING METHOD

(71) Applicant: SYSMEX CORPORATION, Kobe (JP)

(72) Inventors: Takuya Iino, Kobe (JP); Keiko Yoshikawa, Kobe (JP); Kazuya Matsumoto, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 59 days.

(21) Appl. No.: 16/522,026

(22) Filed: Jul. 25, 2019

(65) Prior Publication Data

US 2020/0033365 A1  Jan. 30, 2020

(30) Foreign Application Priority Data

Jul. 27, 2018 (JP) .............................. JP2018-141522
Jul. 27, 2018 (JP) .............................. JP2018-141524

(51) Int. Cl.
  *G01N 33/536* (2006.01)
  *G01N 33/49* (2006.01)
  (Continued)

(52) U.S. Cl.
  CPC ....... *G01N 33/536* (2013.01); *G01N 33/4915* (2013.01); *G01N 33/5308* (2013.01);
  (Continued)

(58) Field of Classification Search
  CPC ............. G01N 33/536; G01N 33/4915; G01N 33/56966; G01N 33/68; G01N 33/54306;
  (Continued)

(56) References Cited

U.S. PATENT DOCUMENTS 5,814,468 A * 9/1998 Siiman ................. G01N 33/566
  435/5
2003/0143631 A1   7/2003 Shirahase et al.
  (Continued)

FOREIGN PATENT DOCUMENTS

JP   2003-261596 A   9/2003
JP   2005-506523 A   3/2005
  (Continued)

OTHER PUBLICATIONS

Pugholm et al. Antibody-Based Assays for Phenotyping of Extracellular Vesicles. BioMed Research International. Article ID 524817. pp. 1-15 (2015).*
  (Continued)

*Primary Examiner* — Gailene Gabel
(74) *Attorney, Agent, or Firm* — Sughrue Mion, PLLC

(57) ABSTRACT

The present disclosure relates to a bioparticle measuring method including detecting a signal from a first measurement sample and a signal from a second measurement sample, wherein the first measurement sample is prepared by mixing a first sample containing a bioparticle sampled from a specimen with a detector capable of binding to the bioparticle and containing a labeled substance, in the presence of an inhibitor capable of binding to the bioparticle and containing none of the labeled substance. The second measurement sample is prepared by mixing a second sample sampled from the same specimen independently from the first sample with the detector, under a condition that the inhibitor is substantially absent. A measurement result is then calculated from the detected signals from the first and second measurement samples.

7 Claims, 11 Drawing Sheets

(51) Int. Cl.
*G01N 33/53* (2006.01)
*G01N 33/543* (2006.01)
*G01N 33/569* (2006.01)
*G01N 33/541* (2006.01)
*G01N 15/14* (2006.01)
*G01N 33/68* (2006.01)

(52) U.S. Cl.
CPC ..... *G01N 33/541* (2013.01); *G01N 33/54306* (2013.01); *G01N 33/54353* (2013.01); *G01N 33/56966* (2013.01); *G01N 15/1404* (2013.01); *G01N 33/68* (2013.01)

(58) Field of Classification Search
CPC ........... G01N 33/54353; G01N 33/541; G01N 33/6854; G01N 15/1404
See application file for complete search history.

(56) References Cited

U.S. PATENT DOCUMENTS

2005/0074851 A1* 4/2005 Lal ..................... C07K 14/705
435/69.1
2016/0320390 A1 11/2016 Newman et al.

FOREIGN PATENT DOCUMENTS

| | | |
|---|---|---|
| JP | 2012-530906 A | 12/2012 |
| WO | 2011/077399 | 6/2011 |
| WO | 2013/073932 A1 | 5/2013 |
| WO | 2017/027622 A1 | 2/2017 |

OTHER PUBLICATIONS

Morten Hjuler Nielsen, et al., "A flow cytometric method for characterization of circulating cell-derived microparticles in plasma", Journal of Extracellular Vesicles, Feb. 4, 2014, pp. 1-12, vol. 3.

Nicolas Arraud et al., "Fluorescence Triggering: A General Strategy for Enumerating and Phenotyping Extracellular Vesicles by Flow Cytometry", NIH Public Access Author Manuscript, vol. 89, No. 2, Apr. 9, 2015, pp. 184-195, ISSN: 1552-4922; Cited in the extended European search report dated Dec. 6, 2019 in a counterpart European patent application.

Atul Asati et al., "Fluorescence Adherence Inhibition Assay: A Novel Functional Assessment of Blocking Virus Attachment by Vaccine-Induced Antibodies", PLOS ONE, vol. 11, No. 2, Feb. 10, 2016, pp. 1-18; Cited in the extended European search report dated Dec. 6, 2019 in a counterpart European patent application.

A. Trummer et al., "Isotype controls in phenotyping and quantification of microparticles: A major source of error and how to evade it", Thrombosis Research, Elsevier, Amsterdam, NL, vol. 122, No. 5, Jan. 1, 2008, pp. 691-700, ISSN: 0049-3848; Cited in the extended European search report dated Dec. 6, 2019 in a counterpart European patent application.

Romaric Lacroix et al., "Overcoming Limitations of Microparticle Measurement by Flow Cytometry", Seminars in Thrombosis and Hemostasis, Thieme Medical Publishers, Inc., US, vol. 36, No. 8, Nov. 1, 2010, pp. 807-818, ISSN: 0094-6176; Cited in the extended European search report dated Dec. 6, 2019 in a counterpart European patent application.

Henar Suárez et al., "A bead-assisted flow cytometry method for the semi-quantitative analysis of Extracellular Vesicles", Scientific Reports, vol. 7, No. 1, Sep. 12, 2017, Cited in the extended European search report dated Dec. 6, 2019 in a counterpart European patent application.

The extended European search report dated Dec. 6, 2019 in a counterpart European application No. 19188490.7.

The Office Action dated May 10, 2022 in a counterpart Japanese patent application No. 2018-141522.

* cited by examiner

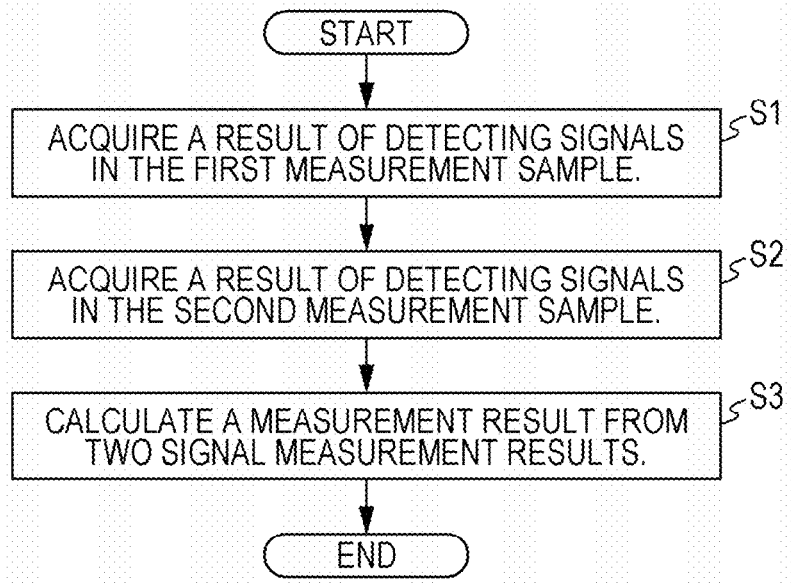
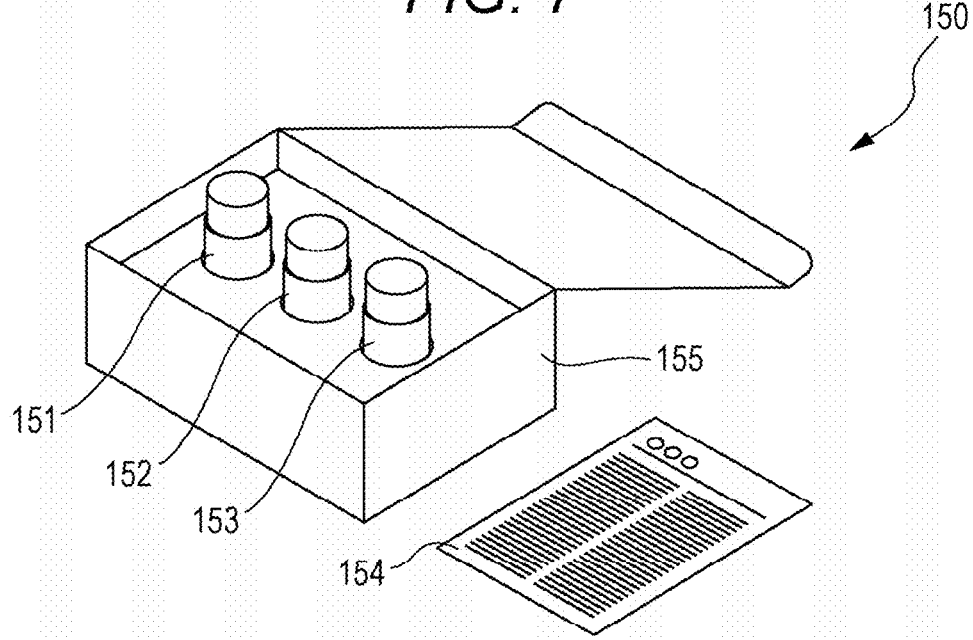

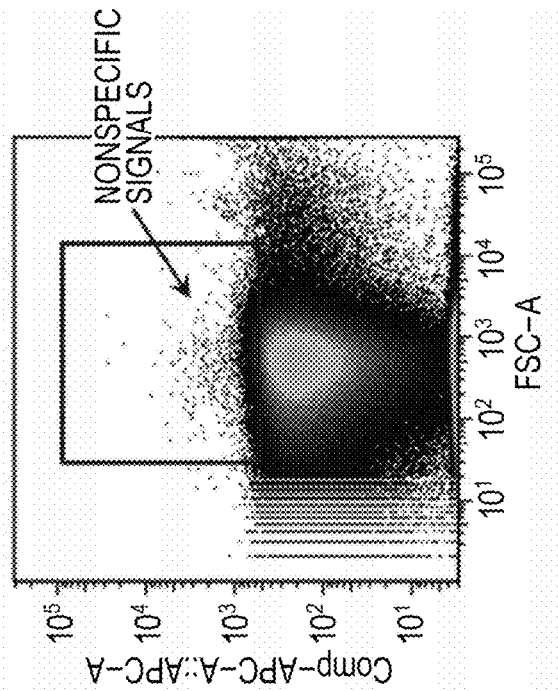
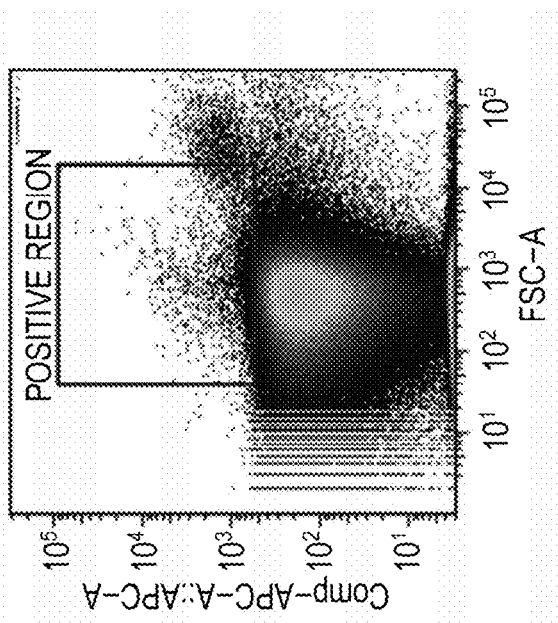

BIOPARTICLE MEASURING METHOD

CROSS REFERENCE TO RELATED APPLICATIONS

This application claims priorities from prior Japanese Patent Application No. 2018-141522 and prior Japanese Patent Application No. 2018-141524, both of which were filed on Jul. 27, 2018, the entire contents of which are incorporated herein by reference.

TECHNICAL FIELD

The present specification discloses a technology regarding a bioparticle measuring method, nonspecific signal detecting method, and a reagent kit for bioparticle measuring method and bioparticle detection.

BACKGROUND

It is known that in the living body, aggregates such as amyloid aggregates, and bioparticles such as various extracellular vesicles called exosomes and microparticles are released from an inside of a cell to an outside of the cell. In recent years, these bioparticles have attracted attention as biomarkers which reflect pathophysiological information of tissues. An example of a method for measuring an extracellular vesicle is "A flow cytometric method for characterization of circulating cell-derived microparticles in plasma, Nielsen M H et al., J Extracell Vesicles. 2014; 3. doi: 10.3402/jev.v3.20795. eCollection 201". This document discloses a method for determining a CD41-positive extracellular vesicle by setting a threshold of a background signal from a fluorescence intensity of a scattergram of an isotype control antibody as a negative control for a labeled antibody.

The inventors have found that, in the method described in "A flow cytometric method for characterization of circulating cell-derived microparticles in plasma, Nielsen M H et al., J Extracell Vesicles. 2014; 3. doi: 10.3402/jev.v3.20795. eCollection 201", there is a possibility that a fluorescent dye-labeled antibody cannot discriminate contaminants other than extracellular vesicles from signals generated through nonspecific binding, and the extracellular vesicles cannot be precisely detected.

SUMMARY

The scope of the present invention is defined solely by the appended claims, and is not affected to any degree by the statements within this summary.

One embodiment of the present disclosure relates to a bioparticle measuring method. The measuring method includes: detecting signal from a first measurement sample and signal from a second measurement sample, wherein the first measurement sample is prepared by mixing: a first sample containing a bioparticle sampled from a specimen; and a detector capable of binding to the bioparticle and containing a labeled substance, in the presence of an inhibitor capable of binding to the bioparticle and containing none of the labeled substance, and the second measurement sample is prepared by mixing: a second sample sampled from the same specimen independently from the first sample; and the detector, under a condition that the inhibitor is substantially absent; and calculating a measurement result of the bioparticle from a detection result of the signals from the first measurement sample and a detection result of the signals from the second measurement sample.

One embodiment of the present disclosure relates to a bioparticle measuring method, comprising a detection step in which signals detected from a measurement sample prepared by: mixing a sample containing a bioparticle; and a detector capable of binding to the bioparticle and containing a labeled substance, in the presence of an inhibitor capable of binding to the bioparticle and containing none of the labeled substance, are determined as nonspecific signals, and signals from the measurement sample are detected by a particle analyzer.

One embodiment of the present disclosure relates to a bioparticle measuring method comprising: a preparation step a-1 for forming a complex (i) comprising a bioparticle, a capturer and an inhibitor on a solid phase by mixing: a sample (i) containing the bioparticle sampled from a specimen; a capturer containing a tag which binds to the solid phase and capable of binding to the bioparticle; and a detector capable of binding to the bioparticle and containing an labeled substance, in the presence of the inhibitor capable of binding to the bioparticle and containing none of the labeled substance; a preparation step a-2 for preparing a measurement sample (i) by dissociating a part or a whole of the complex (i) from the solid phase is prepared; a preparation step b-1 for forming a complex (ii) of the bioparticle, the capturer and the inhibitor on a solid phase by mixing: a sample (ii) sampled from the same specimen in the preparation step a-1 independently from the sample (i), the capturer containing a tag which binds to the solid phase and capable of binding to the bioparticle; and the detector, under a condition that the inhibitor is substantially absent; a preparation step b-2 for preparing a measurement sample (ii) containing a part or a whole of the complex (ii) dissociated from the solid phase; a detection step for detecting by a particle analyzer signals from the measurement sample (i) and signals from the measurement sample (ii); and a calculation step for calculating a measurement result of the bioparticle from a detection result of the signals from the measurement sample (i) and a detection result of the signals from the measurement sample (ii).

BRIEF DESCRIPTION OF THE DRAWINGS

FIG. 6 illustrates a flow chart of operations of the particle measuring device;

FIG. 7 illustrates an example of a test kit;

FIG. 8A illustrates signals detected using an APC-labeled anti-CD235a antibody in accordance with a conventional method. FIG. 8B illustrates signals detected using an APC-labeled isotype control antibody in accordance with a conventional method;

DETAILED DESCRIPTION OF THE PREFERRED EMBODIMENTS

[1. Explanation of Terms]

Figure 1:
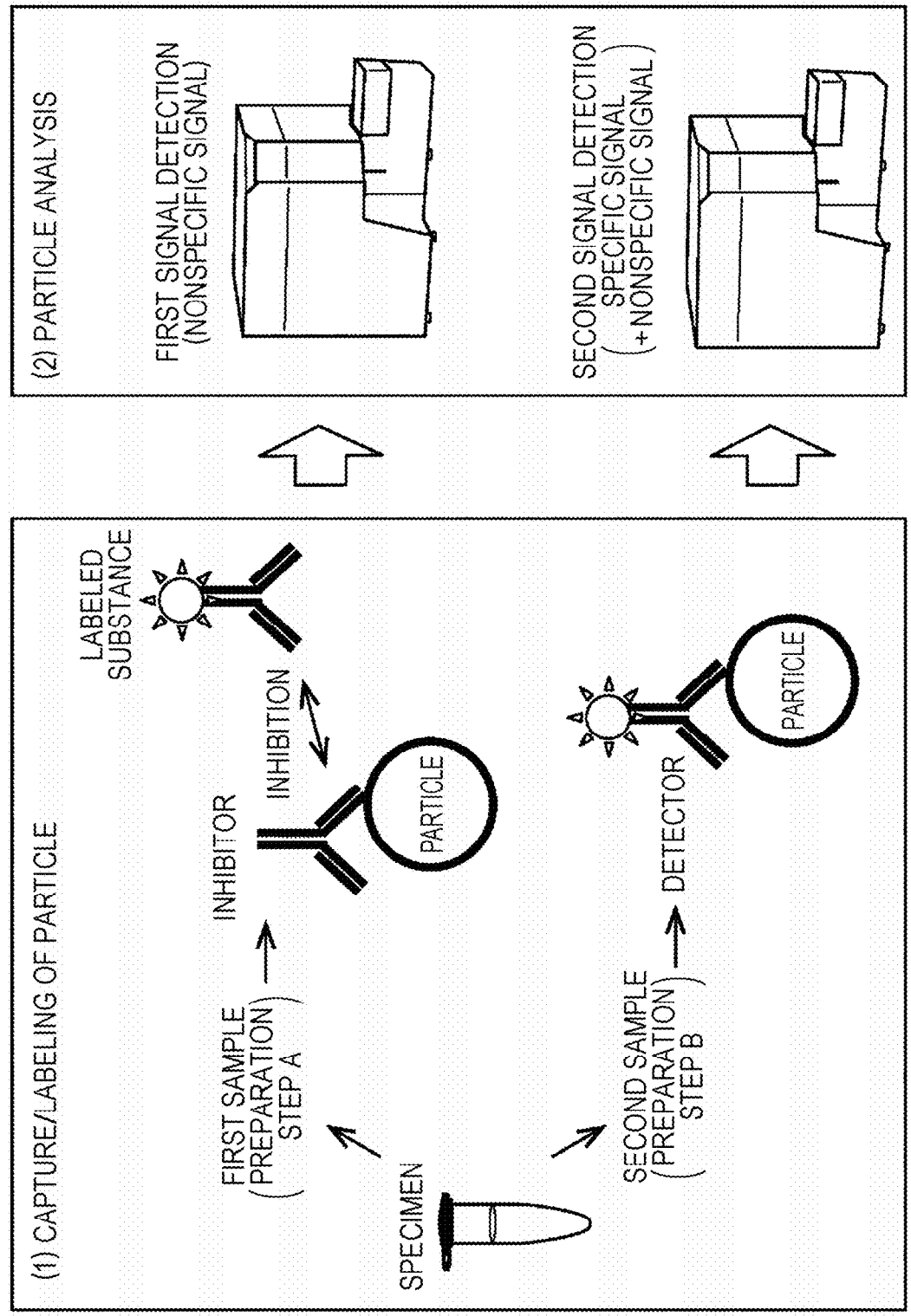
FIG. 1 illustrates a schematic drawing of a first measuring method.

First, terms used in the present disclosure will be explained. Unless otherwise specifically noted, terms used in the specification, claims, and figures are interpreted in accordance with the explanation in this section.

The "specimen" is a liquid component sampled from an animal or a plant. The "specimen" is not limited as long as the specimen contains a bioparticle. Specific examples of a specimen sampled from an animal include serum, plasma, lymph, urine, ascitic fluid, pleural fluid, cerebrospinal fluid, interstitial fluid, and the like. Examples of a liquid sample sampled from a plant include interstitial fluid, xylem sap, phloem sap, and the like. The specimen may be a concentrate or an extract of a bioparticle.

The "bioparticle" is not limited as long as the "bioparticle" is derived from a living body. The bioparticle is e.g. a living body-derived component having a size of about several nm to several thousand nm. Examples of the bioparticle include an amyloid aggregate, a protein aggregate such a tau protein aggregate, a protein, an extracellular vesicle, and the like. The extracellular vesicle is a particle having a size of about several ten nm to several thousand nm and covered with a membrane mainly composed of a phospholipid released from a cell. Examples of the extracellular vesicle include an exosome, a microparticle, an apoptotic body, and the like. In many cases, the extracellular vesicle contains biomolecules. For example, the exosome or the microparticle can contain biomolecules such as polypeptides and nucleic acids (RNA such as mRNA, miRNA, and non-coding RNA). For example, the apoptotic body can contain fragmented nuclei, organelles, and the like. The extracellular vesicle can contain biomolecules such as polypeptides and RNAs. The "polypeptide" is intended as a compound in which a plurality of amino acids are linked through peptide bonds. The "polypeptide" includes proteins having relatively large molecular weights and peptides having relatively small molecular weights Preferably, the bioparticle to be measured has a size of 30 nm or larger. Preferably, the bioparticle has a size of 1,000 nm or smaller.

Preferably, the bioparticle is an extracellular vesicle. For example, the exosome has a size of about 30 to 100 nm. The microparticle has a size of e.g. about 100 to 1000 nm. The size of the particle is preferably expressed in an outer diameter.

A molecule which is present in the bioparticle and is to be measured is also referred to as a target molecule. Examples of the target molecule include a protein, a sugar chain, a lipid, a nucleic acid, and the like. A site present in the target molecule, to which a detector described below binds, is also referred to as "target site". The target site may be a whole bioparticle or a partial bioparticle. When the bioparticle contains a plurality of components like the extracellular vesicle, the target site may be a whole or a part of each component. For example, the target site may be a whole or a part of the target molecule.

The "detector" is a substance which contains a labeled substance and binds to a bioparticle. A specific example of the detector is a labeled "binder" capable of binding to a bioparticle.

The "labeled substance" is not particularly limited as long as detectable signals are generated. For example, the "labeled substance" may be a substance which generates signals by itself (hereinafter, also referred to as a "signal generator"), or a substance which catalyzes a reaction of another substance to generate signals. Examples of the signal generator include a fluorescent substance, a radioactive isotope, and the like. The substance which catalyzes a reaction of another substance to generate detectable signals is e.g. an enzyme. Examples of the enzyme include alkaline phosphatase (ALP), peroxidase, β-galactosidase, luciferase, and the like.

Examples of the fluorescent substance include a fluorescein derivative, a rhodamine derivative, Texas Red, Cy dye, Alexa (registered trademark) Fluor, MegaStokes (trademark) Dye, Oyster (trademark), DyLight (trademark), HiLyte (trademark) Fluor, Brilliant Violet (trademark), Qdot (registered trademark), phycoerythrin (PE), allophycocyanin (APC), PerCP, Tetramethylrhodamine (TRITC), and tandem dyes thereof. More specific examples of the fluorescent substance include fluorescent dyes such as AMCA, Pacific Blue, Alexa Fluor 405, Pacific Orange, Krome Orange, Brilliant Violet 421, Brilliant Violet 510, Brilliant Violet 605, Brilliant Violet 650, Brilliant Violet 711, Brilliant Violet 785, Alexa Fluor 488, Qdot (R) 605, FITC, PE/RD1, ECD/PE-TexasRed, PC5/SPRD/PE-Cy5, PC5.5/PE-Cy5.5, PerCP, PerCP-Cy5.5, PE-Alexa Fluor 700, PC7/PE-Cy7, PE-Alexa Fluor 750, TRITC, Cy3, Alexa Fluor 594, Texas Red, Alexa Fluor 647, Alexa Fluor 700, Cy5, Cy5.5, APC, APC7/APC-Cy7, APC Alexa Fluor 700 and APC Alexa Fluor 750, fluorescent proteins such as Enhanced green fluorescent protein (EGFP), and the like.

Examples of the radioactive isotope include $^{125}I$, $^{14}C$, $^{32}P$, and the like. Above all, the fluorescent dyes are particularly preferable as the labeled substance.

The "binder" is a substance which is a part of the detector and can bind to the bioparticle. Examples of the binder include an antibody, an aptamer, a lectin, and the like. Preferably, the binder can bind to at least the target site. When the binder is an antibody, the target molecule is also called an antigen, but the antigen may include proteins, sugar chains, and the like. Preferably, at least a part of the binder specifically binds to the target site.

The "antibody" may include a polyclonal antibody, a monoclonal antibody and fragments thereof (e.g. Fab, F(ab) 2, Fv fragment, minibody, scFv-Fc, scFv, diabody, triabody, tetrabody, etc.), which are obtained by immunizing a non-human animal with a target protein or a part thereof present on a particle as an antigen. A class and a subclass of an immunoglobulin are not particularly limited.

The target protein as the antigen used for producing the antibody is not limited as long as an antibody for the target protein can be produced. The target protein used as the antigen may be a protein extracted from an animal or a plant in accordance with a known method, or a recombinant protein obtained by a recombinant genetic engineering technique. When a part of the target protein is used as an antigen, a fragment obtained by digesting the target protein with an enzyme or the like may be used, or a peptide having the same sequence as a partial amino acid sequence of the target protein may be used as an antigen. The peptide can be synthesized by a known method.

The "Lectin" is not limited as long as the lectin can bind to a target sugar chain. Examples of the lectin include lectin, galectin, collectin, ficolin, intelectin, annexin, lectican, F-box lectin, fucolectin, tachylectin, leczyme, L-type lectin, M-type lectin, P-type lectin, and R-type lectin.

The "inhibitor" is a substance capable of inhibiting the binding between a target site and a detector. Preferably, the inhibitor is a substance capable of binding to the target site. Examples of the inhibitor includes an antibody, a lectin, and the like. For explaining the antibody and the lectin, the explanation about the binder is cited.

The inhibitor may be a substance which is the same as or different from the binder contained in the detector. For example, when the target site is an antigen epitope and the binder contained in the detector is an antibody, the inhibitor can contain an antibody capable of binding to a target site to which at least the antibody contained in the detector binds. In this case, in the inhibitor, the antibody which binds to the epitope may be a polyclonal antibody or a monoclonal antibody. The inhibitor may be a mixture of an antibody which binds to the target site, and another antibody. Furthermore, when the target site is an antigen epitope and the binder contained in the detector is an antibody, the inhibitor may be an aptamer, a lectin, or the like, which binds to the epitope.

When the target site is a lectin-binding site of a sugar chain and the binder contained in the detector is a lectin, the inhibitor can contain a lectin capable of binding to at least a target site to which the lectin contained in the detector binds. In this case, the lectin contained in the inhibitor may be a mixture of a lectin which binds to the lectin-binding site, and another lectin. Furthermore, when the target site is a lectin-binding site of a sugar chain and the binder contained in the detector is a lectin, the inhibitor may be an antigen which binds to the lectin-binding site.

More preferably, the detector and the inhibitor compete with each other in binding to the bioparticle.

Preferably, the inhibitor contains no labeled substance, or contains a labeled substance different from that of the detector.

A "capturer" is not limited as long as the capturer contains a binder and a tag. The binder contained in the capturer is not limited as long as the binder can bind to the bioparticle. Like the binder contained in the detector, examples of the binder contained in the capturer include an antibody, a lectin, and the like. For explaining the antibody and the lectin, the explanation about the binder contained in detector is cited. Preferably, the binder contained in the capturer has a capturing force to continue to capture bioparticles even after a B/F separation process described later.

Preferably, the binder contained in the capturer does not interfere with the binding between the binder contained in the detector and the bioparticle, and the binding between the binder contained in the inhibitor and the bioparticle. For example, the capturer preferably binds to a site different from the target site which is present on the bioparticle and to which the binder contained in the detector binds.

A tag can binds to a solid phase in a dissociatable manner. The tag directly or indirectly binds to the solid phase. The "indirectly binds to the solid phase" means that the tag binds to the solid phase through another substance. For example, the tag can be immobilized to the solid phase through an immobilizer. The bond between the tag and the immobilizer can be dissociated by adding a dissociator.

Combination of the tag and the immobilizer is known in the art. Examples of the combination include a combination of a biotin (including biotin analogues such as biotin and desthiobiotin) and an avidin (including avidin analogues such as avidin and streptavidin), a combination of nickel and histidine tag, a combination of glutathione and glutathione-S-transferase, a combination of oligonucleotide and its complementary strand, and the like. For example, desthiobiotin can be used as a tag, and avidin or streptavidin can be used as an immobilizer. As another example, a histidine tag can be used as a tag, and nickel can be used as an immobilizer. As another example, a glutathione-S-transferase can be used as a tag, and glutathione can be used as an immobilizer. Furthermore, an oligonucleotide can be used as a tag, and its complementary strand can be used as an immobilizer.

As another aspect, the tag and the immobilizer can also be coupled through a disulfide bond. In this case, the tag and the immobilizer can be dissociated from each other by adding a reducing agent or an enzyme for cleaving an inside or a vicinity of a spacer of the disulfide bond as a dissociator to reduce the disulfide bond or to cleave the inside or the vicinity of the spacer. Examples of the reducing agent include β-mercaptoethanol, dithiothreitol, dithioerythritol, tris(hydroxypropyl) phosphine, tris(2-carboxyethyl) phosphine, and the like.

The dissociator is not limited as long as the dissociator can dissociate the bond between the tag and the immobilizer. As the dissociator, a known molecule can be used. For example, when desthiobiotin is used as a tag and avidin or streptavidin is used as an immobilizer, biotin can be used as a dissociator. Since biotin has a stronger bondability to avidin or streptavidin than that of desthiobiotin, the bond between desthiobiotin and avidin or streptavidin is dissociated in the presence of biotin. When the number or amount of the desthiobiotin molecules is taken as a base of 1, the number or amount of biotin molecules added to a reaction solution is preferably e.g. 1 to 1 trillion times of the desthiobiotin molecules. When the histidine tag is used as a tag and nickel is used as an immobilizer, imidazole can be used as a dissociator. When the glutathione-S-transferase is used as a tag and glutathione is used as an immobilizer, a reduced glutathione can be used as a dissociator. Furthermore, when an oligonucleotide is used as a tag and its complementary strand is used as an immobilizer, a DNase and a low salt concentration-buffer capable of dissociating double bonds of DNA, or the like can be used as a dissociator. In this case, heat denaturation may be carried out instead of the dissociator.

A treatment temperature and a treatment time with the dissociator can be appropriately set depending on the type of the dissociator. Typically, the reaction solution can be allowed to stand or gently stirred at 20 to 45° C. for about 3 minutes to 2 hours. When biotin is used as a dissociator, treatment at 20 to 30° C. for about 30 minutes to 1 hour is preferable.

Methods for preparing a binder containing a tag are known. The tag and the binder may be directly or indirectly coupled.

The solid phase can be selected from known solid phases which are conventionally used in immunological techniques. Examples of materials for such a solid phase include latex, rubber, polyethylene, polypropylene, polystyrene, styrene-butadiene copolymer, polyvinyl chloride, polyvinyl acetate, polyacrylamide, polymethacrylate, a styrene-methacrylate copolymer, polyglycidyl methacrylate, an acrolein-ethylene glycol dimethacrylate copolymer, polyvinylidene difluoride (PVDF), silicone, agarose, gelatin, erythrocyte, silica gel, glass, inert alumina, magnetic material, and the like. One or a plurality of these materials may be combined. Examples of the shape of the solid phase include a microtiter plate, a test tube, a particle, and the like. The particle may be magnetic. Magnetic particles are known in the art. Examples of the magnetic particles include particles containing $Fe_2O_3$ and/or $Fe_3O_4$, cobalt, nickel, ferrite, magnetite, or the like, as a base.

A "flow cytometer" is a device of analyzing particles by introducing the particles into a flow cell and detecting signals (optical signals, electrical signals, etc.) generated from the individual fine particles.

[2. Bioparticle Measuring Method]

[2-1. First Measuring Method]

The first measuring method in the present disclosure relates to a bioparticle measuring method including detecting nonspecific signals using an inhibitor.

An outline of the first measuring method will be explained with reference to FIG. 1.

In FIG. 1 (1), a first sample and a second sample are separately sampled from the same specimen containing a bioparticle. The separately sampling means to sample the first sample and the second sample in each of different containers.

In a preparation step A, a detector is mixed with the first sample in the presence of an inhibitor. The measurement sample prepared in the preparation step A is taken as a first measurement sample.

The aspect of mixing the detector and the first sample in the presence of the inhibitor may include the following four aspects:

i. an aspect that the first sample and the inhibitor are mixed, and then incubated for a certain period, to which subsequently a detection antibody is added;

ii. an aspect that the detector and the inhibitor are mixed, and then the mixture and the first sample are mixed;

iii. an aspect that the first sample and the inhibitor are mixed, to which subsequently the detector is added;

iv. an aspect that the first sample and the detector are mixed, to which subsequently the inhibitor is added.

The aspect of any one of i to iii is preferable.

In the case of the aspect i, the sample which has been added with the detector and then incubated for a certain period can be taken as a first measurement sample.

In the case of the aspect ii, the sample which has been prepared by mixing the mixture of the detector and the inhibitor with the first sample and then incubating the mixture for a certain period can be taken as a first measurement sample.

In the case of the aspect iii or iv, the sample prepared by incubating the mixture of the detector, the inhibitor, and the first sample for a certain period can be taken as a first measurement sample.

In the above description, the certain period may be e.g. about 30 minutes to 2 hours in the case of a temperature of about 20 to 30° C., and about 2 hours to 24 hours in the case of a temperature of about 0 to 10° C.

A mixing ratio of the detector and the inhibitor can be appropriately set depending on the affinity of each binder for the target site. For example, when the number or amount of the binder molecules contained in the detector is taken as a base of 1, the number or amount of the binder molecules contained in the inhibitor can be about 2 to 100 times, preferably 5 to 50 times of the binder molecules contained in the detector.

In a preparation step B, the detector is mixed with the second sample under a condition that the inhibitor is substantially absent. The phrase "the inhibitor is substantially absent" means that the inhibitor is absent or that the inhibitor is present with such a molecular number that does not inhibit the bond between the detector and the bioparticle.

The sample which has been prepared by mixing the detector and the second sample and then incubating the mixture for a certain period can be taken as a second measurement sample. The certain period is as explained in the preparation step A.

The preparation step B can be carried out prior to, or simultaneously with, or after the preparation step A.

Next, in FIG. 1 (2), signals attributed to the labeled substance contained in the first measurement sample and signals attributed to the labeled substance contained in the second measurement sample are detected by a particle analyzer. The particle analyzer can be e.g. a flow cytometer.

When the first measurement sample and the second measurement sample are measured by the particle analyzer, the first measurement sample and the second measurement sample may be directly used, but may be used after dilution. In the case of dilution, for example, a buffer such as PBS known in the art can be used. The dilution ratio can be e.g. 5 to 20 times, preferably 10 to 15 times.

For detecting the bioparticle, the size of the particle should be taken into consideration. For this reason, the condition for detecting the particle in the flow cytometer is also preferably set to a condition making it possible to detect particles having several tens nm sizes.

For example, the flow rate for flowing the first measurement sample and the second measurement sample into the flow cytometer is preferably about 12 µl/min. When detecting the bioparticle, a photomultiplier voltage can be e.g. about 550 V in a case that a forward scattered light (FSC) is about 700 V, a side-scattered light (SSC) is about 320 V, and a fluorescent dye is a fluorescein derivative, and can be about 500 V in a case that the fluorescent dye is allophycocyanin (APC). A threshold of the SSC can be about 200 V.

Since the inhibitor inhibits the bond between the detector and the bioparticle in the first measurement sample, the bioparticle to be fundamentally detected by the detector is not detected. Thus, the signals attributed to the labeled substance contained in the first measurement sample are supposed to be nonspecific signals. The signals attributed to the labeled substance contained in the second measurement sample are supposed to include specific signals and nonspecific signals.

The results calculated from the detection result of the signals attributed to the labeled substance contained in the first measurement sample and the detection result of the signals attributed to the labeled substance contained in the second measurement sample can be supposed to measurement results based on the specific reaction between the bioparticle and the detector. Specifically, the measurement results based on the specific reaction between the bioparticle and the detector can be calculated by subtracting the detection result of the signals attributed to the labeled substance contained in the first measurement sample from the detection result of the signals attributed to the labeled substance contained in the second measurement sample.

[2-2. Second Measuring Method]

The second measuring method refers to a bioparticle measuring method, in which a complex of the bioparticle and the detector is formed on the solid phase, then the complex of the bioparticle and the detector is dissociated from the solid phase, and the dissociated complex of the bioparticle and the detector is used as a measurement sample.

An outline of the second measuring method will be explained with reference to FIG. 2.

Figure 2:
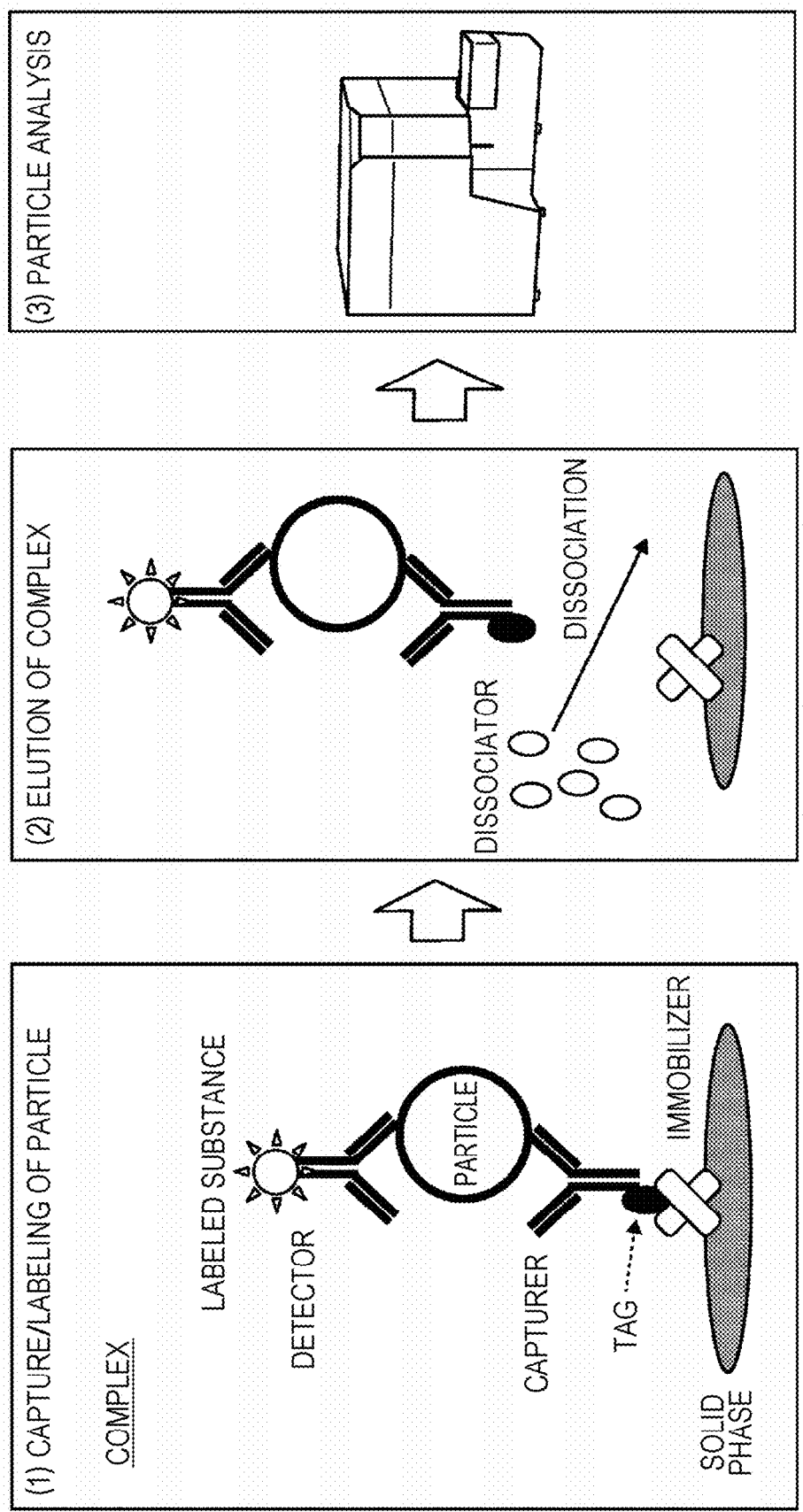
FIG. 2 illustrates a schematic drawing of a second measuring method.

As shown in FIG. 2 (1), in the second measuring method, first, a complex of the bioparticle and the detector is formed on a solid phase. For example, in the second measuring method, the capturer is added to the solid phase on which the immobilizer is immobilized. The capturer is brought into contact with the solid phase for a certain period. After the contact, B/F separation may be carried out to remove unreacted capturers which have not bound to the immobilizer. Next, as a sample, an undiluted solution of the specimen or a diluted solution obtained by diluting the specimen with PBS or the like is brought into contact with the capturer bound to the immobilizer for a certain period, and the bioparticle in the sample is captured by the capturer immobilized on the solid phase. After the contact, B/F separation may be carried out to remove sample components which have not bound to the capturer. Subsequently, the particle captured by the capturer are brought into contact with the detector for a certain period. After the contact, B/F separation may be carried out to remove unreacted detectors which have not bound to the bioparticle. The B/F separation is intended to remove the unreacted components.

As shown in FIG. 2 (2), the dissociator is brought into contact with a detection antibody-bioparticle-capturer complex immobilized on the solid phase for a certain period to dissociate the detection antibody-bioparticle-capturer complex from the solid phase. In this step, it is only necessary to dissociate at least a part of the detection antibody-bioparticle-capturer complex formed on the solid phase.

As shown in FIG. 2 (3), as a measurement sample, the dissociated detection antibody-bioparticle-capturer complex is measured with the particle analyzer.

In this section, the certain period may be e.g. about 1 second to 2 hours in the case of a temperature of about 20 to 30° C., and about 1 second to 24 hours in the case of a temperature of about 0 to 10° C.

The particle analyzer is preferably a flow cytometer. For a condition for measuring the detection antibody-bioparticle-capturer complex, the explanation in the section 2-1 is cited.

[2-3. Third Measuring Method]

In the third measuring method, the first measuring method and the second measuring method are combined.

An outline of the third measuring method will be explained with reference to FIG. 3.

Figure 3:
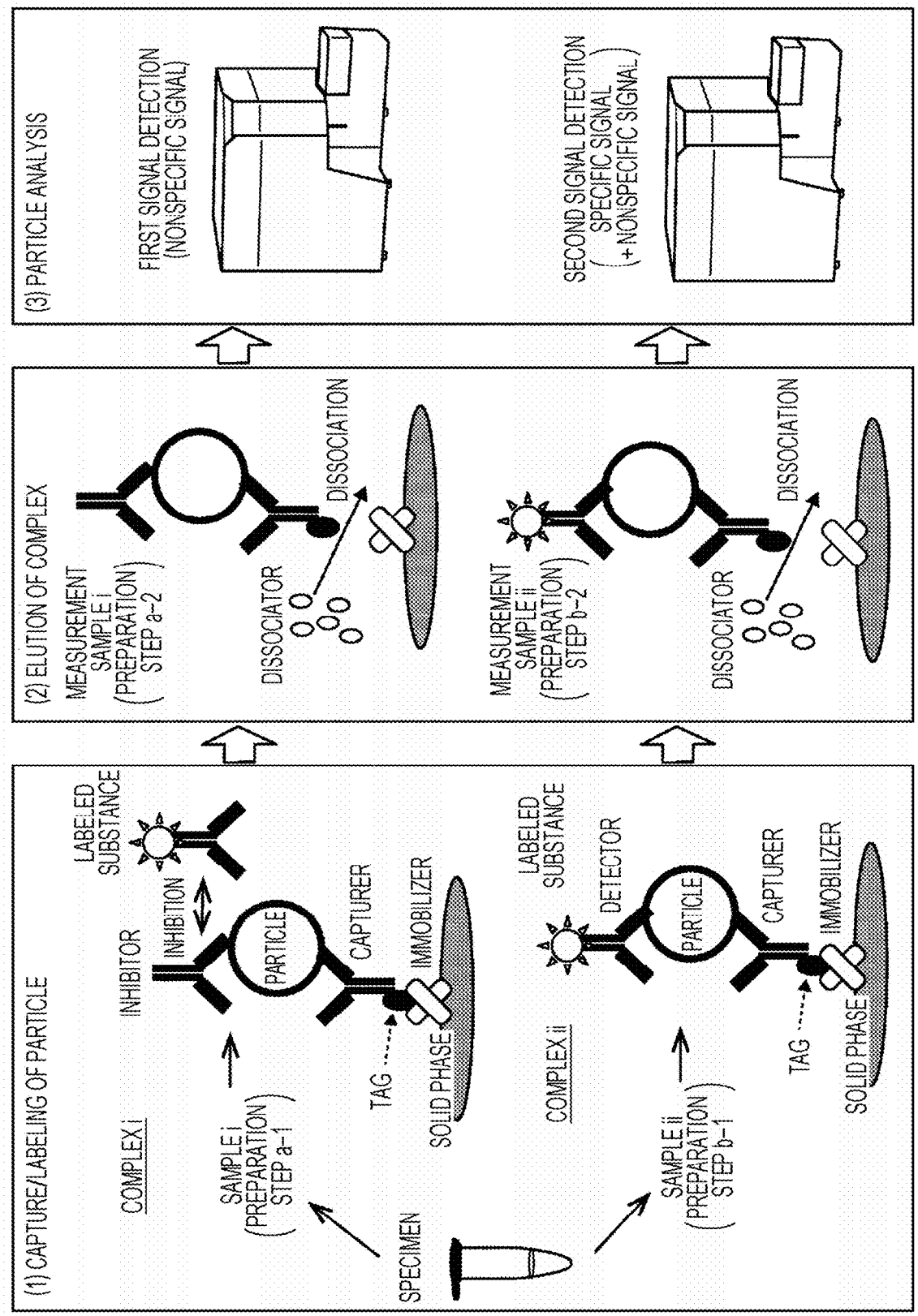
FIG. 3 illustrates a schematic drawing of a third measuring method.

As shown in FIG. 3 (1), in the third measuring method, a sample i containing a bioparticle sampled from a specimen, a capturer, and a detector are mixed in the presence of an inhibitor to form a complex i of the bioparticle, the capturer, and the inhibitor on a solid phase (preparation step a-1).

Next, as shown in FIG. 3 (2), a measurement sample i containing a part or a whole of the complex i dissociated from the solid phase using a dissociator is prepared (preparation step a-2).

As shown in FIG. 3 (1), prior to, or simultaneously with, or after the preparation step a-1, a sample ii sampled from the same specimen as described above independently from the sample i, a capturer, and the detector are mixed under a condition that the inhibitor is substantially absent, to form a complex ii of the bioparticle, the capturer, and the inhibitor on the solid phase (preparation step b-1).

Next, as shown in FIG. 3 (2), a measurement sample ii containing a part or a whole of the complex ii dissociated from the solid phase is prepared (preparation step b-2).

Subsequently, signals attributed to a labeled substance contained in the measurement sample i and signals attributed to a labeled substance contained in the measurement sample ii are detected by the particle analyzer.

Furthermore, a measurement result of the bioparticle are calculated from a detection result of the signals attributed to the labeled substance contained in the measurement sample i and a detection result of the signals attributed to the labeled substance contained in the measurement sample ii.

For explaining the formation of the complex i and the complex ii, the explanations in the sections 2-1 and 2-2 are cited. For explaining a method of calculating the results of the signal detection and measurement with the particle analyzer, the explanation in the section 2-1 is cited.

[3. Nonspecific Signal Detecting Method]

The present disclosure includes a nonspecific signal detecting method. The nonspecific signal detecting method includes a detection step. In the detection step, the sample containing the bioparticle sampled from the specimen described in the section 2-1, and a detector are mixed in the presence of an inhibitor capable of binding to the bioparticle and containing none of the labeled substance to prepare a measurement sample. Then signals detected from the measurement sample are determined as nonspecific signals, and signals attributed to the labeled substance contained in the measurement sample are detected by the particle analyzer.

For explaining the measurement sample preparing method, and the signal detecting method with the particle analyzer, the explanation in the section 2-1 is cited.

[4. Particle Measuring Device]

[4-1. Configuration of Device]

A particle measuring device 10 includes at least a processing section 101 and a storage section. The storage section is composed of a main storage section 102 and/or an auxiliary storage section 104. The device 10 may be intended to achieve the methods described in claims 1 to 13. For explaining the device 10 and operation of the device 10, in relation to terms in common with the terms explained in the section 2-1, the explanation in the section 2-1 is cited.

Figure 4:
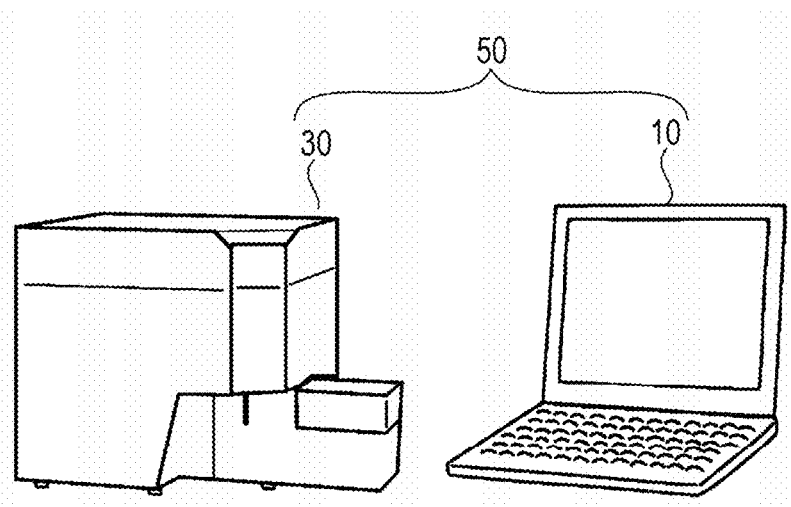
FIG. 4 illustrates a configuration example of a particle measuring system.
Figure 5:
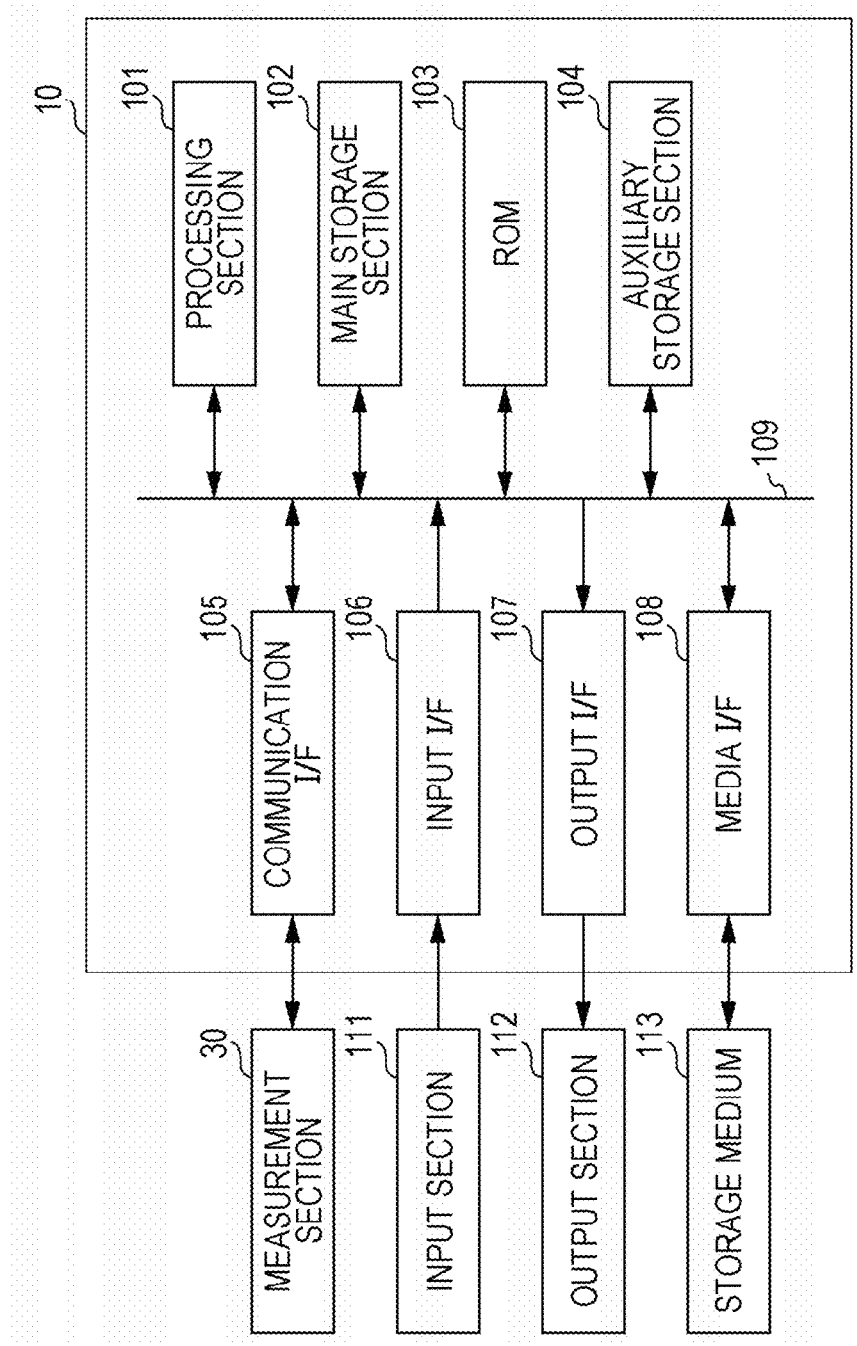
FIG. 5 illustrates a configuration example of a hardware for a particle measuring device.

FIG. 4 and FIG. 5 show configurations of the device 10. The device 10 may be connected to an input section 111, an output section 112, and a storage medium 113. The device 10 may be connected to a measurement section 30 e.g. a particle analyzer such as a flow cytometer. In other words, the device 10 constitutes a particle measuring system 50 connected to the measurement section 30 directly or through a network or the like in some cases.

In the device 10, the processing section 101, the main storage section 102, a read only memory (ROM) 103, the auxiliary storage section 104, a communication interface (I/F) 105, an input interface (I/F) 106, an output interface (I/F) 107, and a media interface (I/F) 108 are connected communicatably with each other through a bus 109.

The processing section 101 is composed of a CPU, an MPU, a GPU, or the like. The processing section 101 executes a computer program stored in the auxiliary storage section 104 or the ROM 103, and the device 10 functions by processing the acquired data. The processing section 101 acquires a result of measuring the signals attributed to the labeled substance contained in the first measurement sample described in the section 2-1 by the particle analyzer, and a result of detecting the signals attributed to the labeled substance contained in the second measurement sample by the particle analyzer. From the two detection results, the measurement result of the bioparticle is calculated.

The ROM 103 is composed of a mask ROM, a PROM, an EPROM, an EEPROM, or the like, in which a computer program to be executed by the processing section 101, and data used for the computer program are recorded. At start-up of the device 10, the ROM 103 stores a boot program executed by the processing section 101, a program regarding an operation of a hardware of the device 10, and settings.

The main storage section 102 is composed of a random access memory (RAM) such as a SRAM or a DRAM. The main storage section 102 is used for reading the computer programs recorded in the ROM 103 and the auxiliary storage section 104. The main storage section 102 is used as a work area of the processing section 101 for executing these computer programs. The main storage section 102 temporarily stores the detection result of the signals acquired through the network, and the like.

The auxiliary storage section 104 is composed of a hard disk, a semiconductor memory element such as a flash memory, an optical disk, or the like. The auxiliary storage section 104 stores various computer programs to be executed by the processing section 101, such as an operating system and an application program, and various setting data to be used for executing the computer programs. Specifically, the detection result of the signals, and the like are stored in a non-volatile manner.

The communication I/F 105 is composed of a serial interface such as USB, IEEE1394 and RS-232C, a parallel interface such as SCSI, IDE and IEEE1284, an analog interface composed of a D/A converter, an A/D converter, or the like, a network interface controller (NIC), and the like. The communication I/F 105 receives data from the measurement section 30 or another external apparatus under the control of the processing section 101. The communication I/F 105 transmits or displays information stored or generated by the device 10 to the measurement section 30 or the outside, as needed. The communication I/F 105 may communicate with the measurement section 30 or another external apparatus (not illustrated in the figure, e.g. another computer or a cloud system) through a network.

The input I/F 106 is composed of e.g. a serial interface such as USB, IEEE1394 and RS-232C, a parallel interface such as SCSI, IDE and IEEE1284, an analog interface composed of a D/A converter, an A/D converter, or the like, and the like. The input I/F 106 accepts character input, click, voice input, and the like from the input section 111. The accepted input contents are stored in the main storage section 102 or the auxiliary storage section 104.

The input section 111 is composed of a touch panel, a keyboard, a mouse, a pen tablet, a microphone, and the like. The input section 111 performs character input or voice input on the device 10. The input section 111 may be connected to the device 10 from the outside or may be integrated with the device 10.

The output I/F 107 is composed of e.g. the same interface as of the input I/F 106. The output I/F 107 outputs information generated by the processing section 101 to the output section 112. The output I/F 107 outputs information generated by the processing section 101 and stored in the auxiliary storage section 104 to the output section 112.

The output section 112 is composed of e.g. a display, a printer, and the like. The output section 112 displays the measurement result transmitted from the measurement section 30, various operation windows in the device 10, the analysis result, and the like.

The media I/F 108 reads e.g. an application software or the like stored in the storage medium 113. The read application software or the like is stored in the main storage section 102 or the auxiliary storage section 104. The media I/F 108 writes information generated by the processing section 101 into the storage medium 113. The media I/F 108 writes information generated by the processing section 101 and stored in the auxiliary storage section 104 into the storage medium 113.

The storage medium 113 is composed of a flexible disk, a CD-ROM, a DVD-ROM, or the like. The storage medium 113 is connected to the media I/F 108 by a flexible disk drive, a CD-ROM drive, a DVD-ROM drive, or the like. The storage medium 113 may store an application program or the like for the computer to execute an operation.

The processing section 101 may acquire an application software and various settings required for controlling the device 10 through a network instead of reading from the ROM 103 or the auxiliary storage section 104. The application program is stored in the auxiliary storage section of the server computer on the network, the device 10 accesses the server computer to download a computer program, and the computer program can also be stored in the ROM 103 or the auxiliary storage section 104.

The ROM 103 or the auxiliary storage section 104 is installed with e.g. an operating system for providing a graphical user interface environment, such as Windows (registered trademark) manufactured and sold by Microsoft Corporation, USA. The application program according to the second embodiment operates on the operating system. That is, the device 10 may be a personal computer or the like.

[4-2. Operation of Device]

Next, an example of the operation of the device 10 will be explained with reference to FIG. 6. The operation of the device 10 is controlled by the processing section 101 of the device 10 in accordance with the computer program which makes the computer execute steps for calculating a detection result of the bioparticle described later.

The processing section 101 acquires a result of measuring the signals attributed to the labeled substance contained in the first measurement sample described in the section 2-1 by the particle analyzer in accordance with a command of start-up input from the input section 111 by the examiner or the like (step S1).

The processing section 101 acquires a result of measuring the signals attributed to the labeled substance contained in the second measurement sample described in the section 2-1 by the particle analyzer (step S2). The order of performing the step S1 and step S2 is not limited. Step S2 may be performed first, or step S1 and step S2 may be simultaneously performed.

The processing section 101 calculates a measurement result of the bioparticle from the two detection results including the detection result of the signals obtained in step S1 and the detection result of the signals obtained in step S2. Specifically, the measurement result of the bioparticle is calculated (step S3) by subtracting the detection result of the signals obtained in step S1 from the detection result of the signals obtained in step S2, and the treatment is terminated.

After step S3, the processing section 101 may store the measurement result of the bioparticle into the auxiliary storage section 104, may output the result to the output section 112, and/or may transmit the result to the external apparatus (not illustrated in the figure).

[5. Program, and the Computer Program-Storing Storage Medium]

The computer program makes the computer execute the steps S1 to S3. The computer program causes the computer to function as the particle measuring device 10.

The computer program may be stored in a storage medium. That is, the computer program is stored in a storage medium e.g. a hard disk, a semiconductor memory element such as a flash memory, an optical disk, or the like. The computer program may be stored in a storage medium connectable with a network such as a cloud server. The computer program may be a program product which is of a download type or stored in a storage medium.

A format for storing the program into the storage medium is not limited as long as the presentation device can read the program. The program is preferably stored into the storage medium in a non-volatile manner.

[6. Test Kit]

[6-1. First Test Kit]

A test kit contains a detector and an inhibitor. FIG. 7 illustrates a schematic drawing of a kit 150.

The kit 150 may include a container 151 for containing the detector, a container 152 for containing the inhibitor, and the reagent kit 150 may include an instruction manual 154 or a sheet 154 describing a URL at which the instruction manual can be browsed. Furthermore, the reagent kit 150 may include a box 155 housing these containers. The kit 150 may include a container 151 for containing a capturer. Although not illustrated in the figure, the kit may include a solid phase for immobilizing the capturer.

The test kit is used to carry out the methods described in the sections 2-1, 2-3, and 3.

[6-2. Second Test Kit]

A test kit includes the detector and the capturer. FIG. 7 illustrates a schematic drawing of a kit 150.

The kit 150 may include the container 151 for containing the detector, the container 152 for containing the container 151 for containing the capturer, and the reagent kit 150 may include the instruction manual 154 or the sheet 154 describing the URL at which the instruction manual can be browsed. Furthermore, the reagent kit 150 may include a box 155 housing these containers. The kit 150 may include the container 151 for containing the inhibitor. Although not illustrated in the figure, the kit may include a solid phase for immobilizing the capturer.

The test kit is used to carry out the methods described in the sections 2-2 and 2-3.

Although the device 10, the operation of the device 10, the computer program, and the test kit have been explained in detail with reference to the attached figures, the present disclosure is not limited to the specific embodiments described above. The embodiments can be modified based on the description in the present specification and the technical knowledge of those skilled in the art.

EXAMPLES

Hereinafter, contents of the present disclosure will be explained in more detail with reference to examples, but the present disclosure should not be interpreted only by examples.

[Material and Method]

(1) Antibody

The antibodies shown in the following Table 1 were used for this study. An unlabeled antibody was used as the inhibitor, and a fluorescence-labeled antibody of the same clone as the unlabeled antibody was used as the detector.

TABLE 1

| Antigen | Clone | Label | Manufacturer | Lot No. |
| --- | --- | --- | --- | --- |
| CD146 | P1H12 | APC | BioLegend | 361016 |
| CD61 | VI-PL2 | FITC | BioLegend | 336404 |
| CD235a | HIR2 | APC | BioLegend | 306608 |
| Isotype control IgG2b | MPC-11 | APC | BioLegend | 400320 |

(2) Plasma Specimen

Plasma prepared in accordance with the following protocol was purchased from ProMedDx LLC. (agency: SUNFCO LTD.).

Blood was sampled in a blood collecting tube containing 3.2% citric acid from six healthy persons. Subsequently, within 15 minutes, the blood was centrifuged at 1500 RCF for 15 minutes. After collecting the supernatant, the supernatant was freeze-stored at −20° C. After delivery, the supernatant was immediately stored at −80° C.

After thawing six specimens of the healthy persons in running water, the specimens were mixed, which was used for analysis.

(3) Culture of Model Cell

As a model cell, HUVEC was used. HUVEC was cultured in an endothelium growth medium (EGM) supplemented with 2% fetal bovine serum. A culture supernatant containing an extracellular vesicle was collected once the cell reached 80% confluent state. The culture supernatant in an amount equivalent to 20 ml was centrifuged at 1,500 RCF for 15 minutes to collect the supernatant, which was further centrifuged at 20,000 RCF for 30 minutes to prepare a cultured cell-derived extracellular vesicle.

(4) Sample for Analysis

A sample for analysis was prepared by mixing 100 μl of the aforementioned plasma and the cultured cell-derived extracellular vesicle collected from 1 ml of the culture supernatant.

(5) Flow Cytometry

Flow cytometry was carried out using FACS Verse (Becton, Dickinson and Company). Each reaction solution diluted with PBS was subjected to measurements under the conditions shown in Table 2 to obtain scattergrams of fluorescence intensity and FSC. In Table 2, the FSC represents a forward□scattered light, and the SSC represents a side-scattered light. A flow rate during the measurement was set to 12 μl/min, and a measurement time was set to 1 minute.

TABLE 2

| Measurement item | Voltage [V] | Threshold [V] |
| --- | --- | --- |
| FSC | 700 | |
| SSC | 320 | 200 |
| FITC | 550 | |
| APC | 500 | |

[Reference Example]

1. Detection of Particle by Conventional Method

An APC-labeled anti-CD235a antibody was used as a detector. An APC-labeled Isotype control IgG2b was used as an isotype control (negative antibody control).

To 12.5 μl of plasma prepared in the section (2) in [Materials and Methods], 0.125 μg of the APC-labeled anti-CD235a antibody or the isotype control antibody was added. Then they are brought into contact with each other for 20 minutes. This reaction solution was diluted 14 times with PBS to prepare a measurement sample.

Flow cytometry was carried out using FACS Verse (Becton, Dickinson and Company). Each reaction solution diluted with PBS was subjected to measurements under the conditions shown in Table 3 to obtain scattergrams of fluorescence intensity and FSC. In Table 3, the FSC represents a forward□scattered light, and the SSC represents a side-scattered light. A flow rate during the measurement was set to 12 μl/min, and a measurement time was set to 1 minute.

TABLE 3

| Measurement item | Voltage [V] | Threshold [V] |
|---|---|---|
| FSC | 700 | |
| SSC | 320 | 200 |
| APC | 500 | |

2. Results

FIG. 8 presents the results obtained by the flow cytometer. FIG. 8A illustrates signals detected using an APC-labeled anti-CD235a antibody. FIG. 8B illustrates signals detected using an APC-labeled isotype control antibody. An area within a positive region frame shown in FIG. 8A is a positive region in which positive signals fundamentally attributed to the CD235a on the extracellular vesicle are detected. In FIG. 8B, signals which could not be fundamentally detected within this region were detected. From this, the inventors considered that nonspecific signals were included in the positive region determined in accordance with the conventional method.

EXAMPLES

1. Example 1

An inhibitor was reacted with an extracellular vesicle in the sample prior to a detector to examine an inhibitory effect.
1-1. Reaction Between Extracellular Vesicle and Detection Antibody In the reaction between the extracellular vesicle and the detection antibody, 1 to 2 μl (equivalent to 0.1 μg) of detection antibody was added to 10 μl of sample, which was prepared so that the total volume was 11 to 12 μl.

Into six tubes, 10 μl of each sample prepared in the section (4) in [Materials and Methods] was dispensed, and 1 μg of each of unlabeled anti-CD146 antibody, anti-CD61 antibody and anti-CD235a antibody shown in Table 1 was added to three tubes out of the six tubes, which were incubated for 1 hour. The remaining 3 tubes were incubated without adding antibodies for 1 hour.

The culture cell-derived extracellular vesicle prepared in the section (3) in [Materials and Methods] was also diluted with PBS in a one-tenth volume of the culture supernatant used, and then 10 μl of the each diluent was dispensed into two tubes. One tube was added with 1 μg of unlabeled anti-CD146 antibody, the other one was added with no additive. The tubes were incubated for 1 hour.

Furthermore, 10 μl of each plasma prepared in the section (2) in [Materials and Methods] was dispensed into two tubes. One tube was added with 1 μg of unlabeled anti-CD146 antibody, the other one was added with no additive. The tubes were incubated for 1 hour.

A tube containing an unlabeled anti-CD146 antibody was added with 0.1 μg of fluorescence-labeled anti-CD146 antibody, a tube containing an unlabeled anti-CD61 antibody was added with 0.1 μg of fluorescence-labeled anti-CD61 antibody, and a tube containing an unlabeled anti-CD235a antibody was added with 0.1 μg of fluorescence-labeled anti-CD235a antibody. Also, to three tubes containing no unlabeled antibody, 0.1 μg of each of the fluorescence-labeled anti-CD146 antibody, anti-CD61 antibody and anti-CD235a antibody was added. Also, to the tubes into which plasma or culture supernatant were dispensed, 0.1 μg of each fluorescence-labeled anti-CD146 antibody was added. The fluorescence-labeled antibody was added to the tubes, which were subsequently incubated for 30 minutes.

Figure 9:
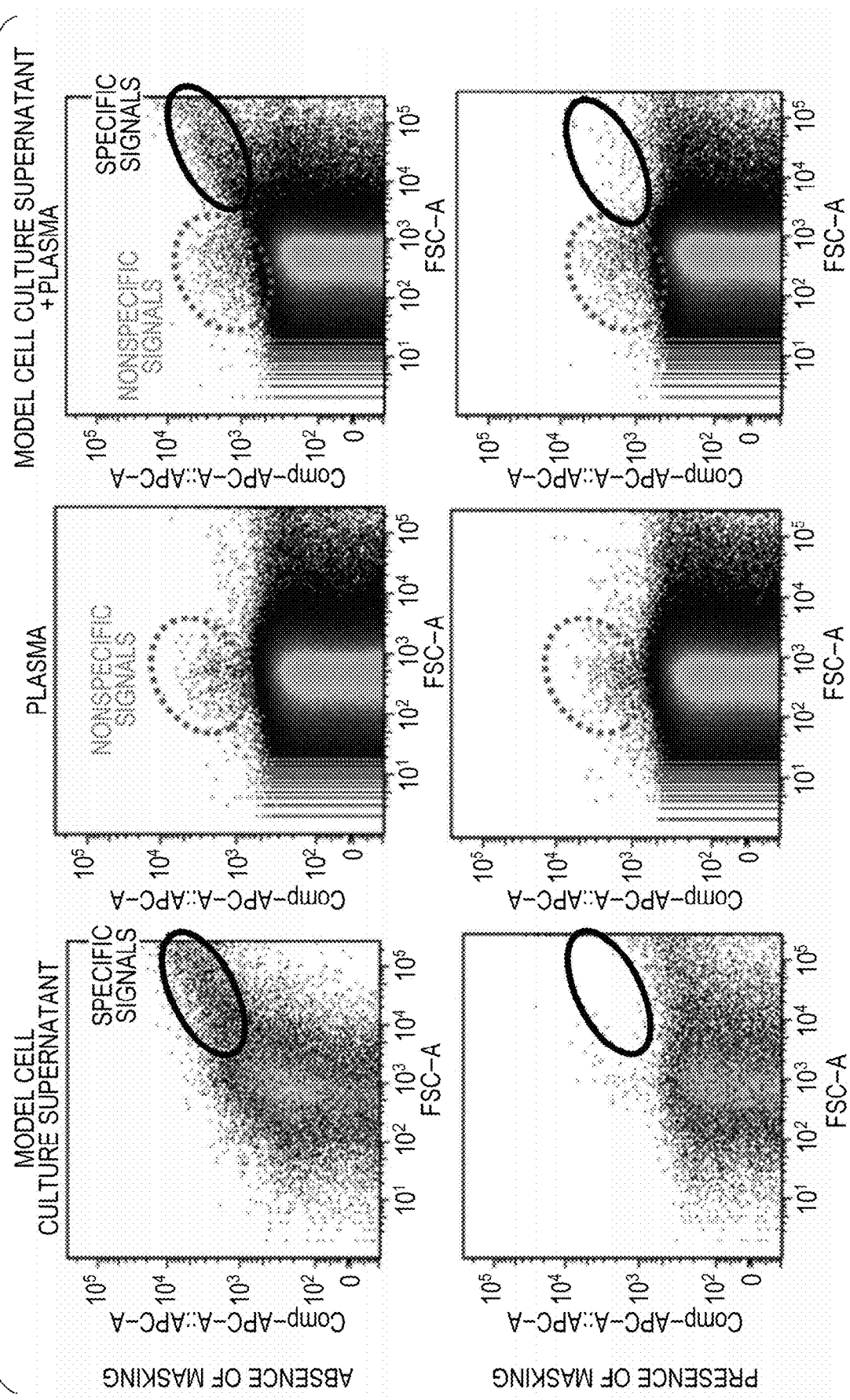
FIG. 9 illustrates results of flow cytometry of an extracellular vesicle using an anti-CD146 antibody.

After completion of the incubation, each reaction solution was diluted 14 times with PBS. Each reaction solution was subjected to flow cytometry. The measurement conditions for flow cytometry were in accordance with the section (5) in [Materials and Methods].
1-2. Results FIG. 9 illustrates results of flow cytometry of the extracellular vesicle using the anti-CD146 antibody. The inhibition by the unlabeled anti-CD146 antibody remarkably decreased the signals (parts surrounded by the solid line on the lower column) compared to the measurement without inhibition. It is supposed that the reason of this result was because the inhibition prevented the fluoresce-labeled anti-CD146 antibody from binding to the target molecule, resulting in no detection of signals.

On the other hand, in the measurement result of the plasma sample, the parts surrounded by the dotted line similarly showed the signals regardless of the presence of the inhibitor. The signals in the parts surrounded by the dotted line were considered to be nonspecific signals unrelated to the CD146 because of free of influence from the inhibition by the anti-CD146 antibody.

Figure 10:
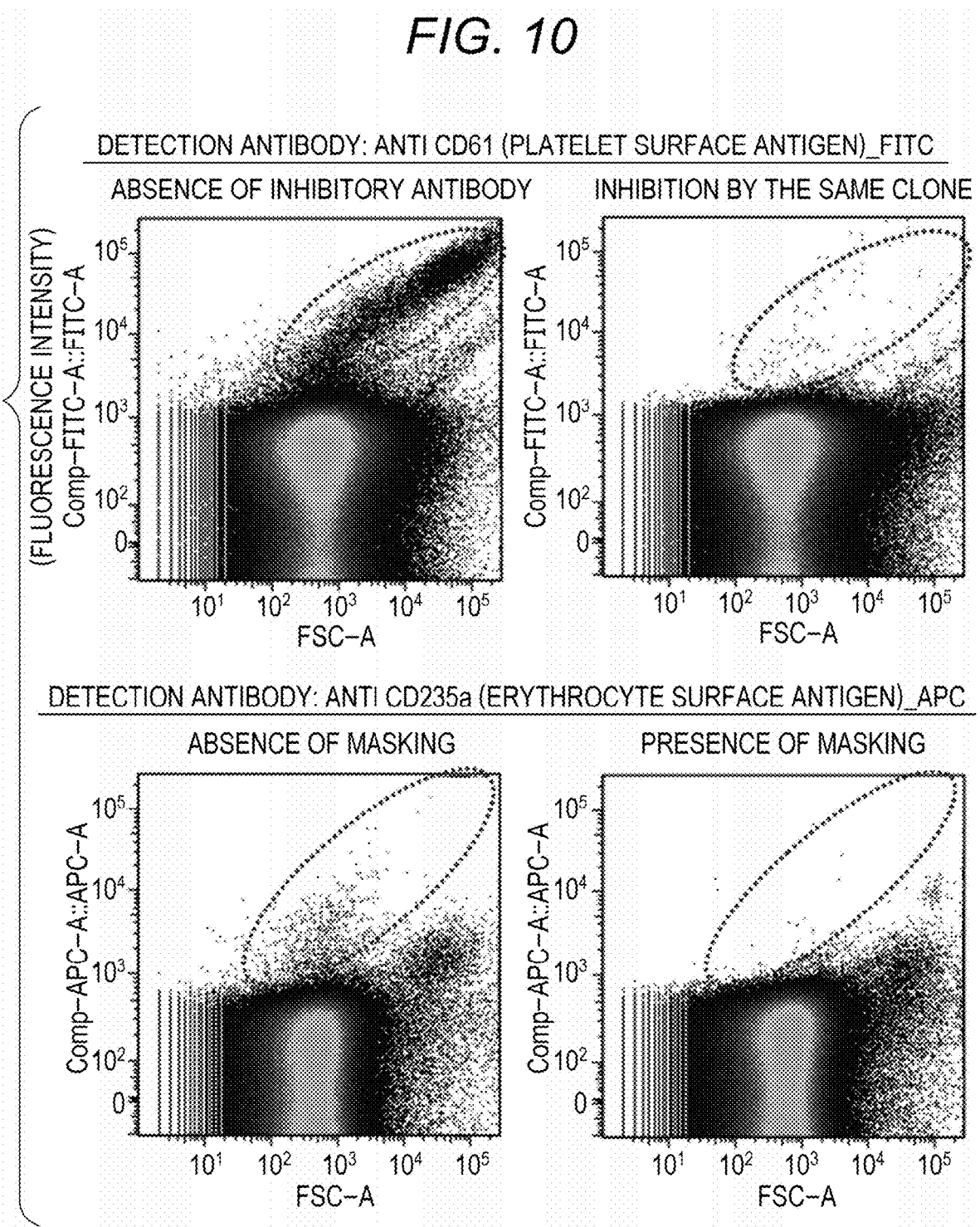
FIG. 10 illustrates results of flow cytometry of the extracellular vesicle using an anti-CD61 antibody or an anti-CD235a antibody.

FIG. 10 illustrates results of flow cytometry of the extracellular vesicle using the anti-CD61 antibody or the anti-CD235a antibody. Both the anti-CD61 antibody and the anti-CD235a antibody showed similar inhibitory effects, and it was possible to discriminate between specific signals and nonspecific signals.

These results showed that the specific signals and the nonspecific signals could be discriminated and analyzed by comparing between the measurement result through the inhibition treatment and the measurement result without the inhibition treatment.

Thus, it was supposed that a true measurement value could be obtained by subtracting the measurement value of the bioparticle signals obtained from the measurement sample through the inhibition from the measurement value of the bioparticle signals obtained from the measurement sample without the inhibition.

2. Example 2

The detection antibody was reacted with the sample in the presence of the unlabeled antibody as an inhibitor to examine the inhibitory effect.
2-1. Reaction Between Extracellular Vesicle and Detection Antibody In relation to the sections (1) Anti-CD61 Antibody, (2) Plasma Specimen, (3) Culture of Model Cell, (4) Sample for Analysis, and (5) Flow Cytometry in [Materials and Methods], the same applies to this section.

Next, the ratio of the unlabeled antibody to the detection antibody was changed to examine the inhibitory effect.

Into 4 tubes, 10 μl of each sample prepared in the section 1-1. (4) was dispensed. To each tube, a solution prepared by mixing each of 0 μg (no unlabeled antibody) of, 0.5 μg (5 times the amount of unlabeled antibody) of, 1 μg (10 times the amount of unlabeled antibody) of, 10 μg (100 times the amount of unlabeled antibody) of unlabeled anti-CD61 antibody, and 0.1 μg of fluorescence-labeled anti-CD61 antibody, shown in Table 1, was added, which was incubated for 1 hour.

After completion of the incubation, each reaction solution was diluted 14 times with PBS. Each reaction solution was subjected to flow cytometry.

2-2. Results

Figure 11:
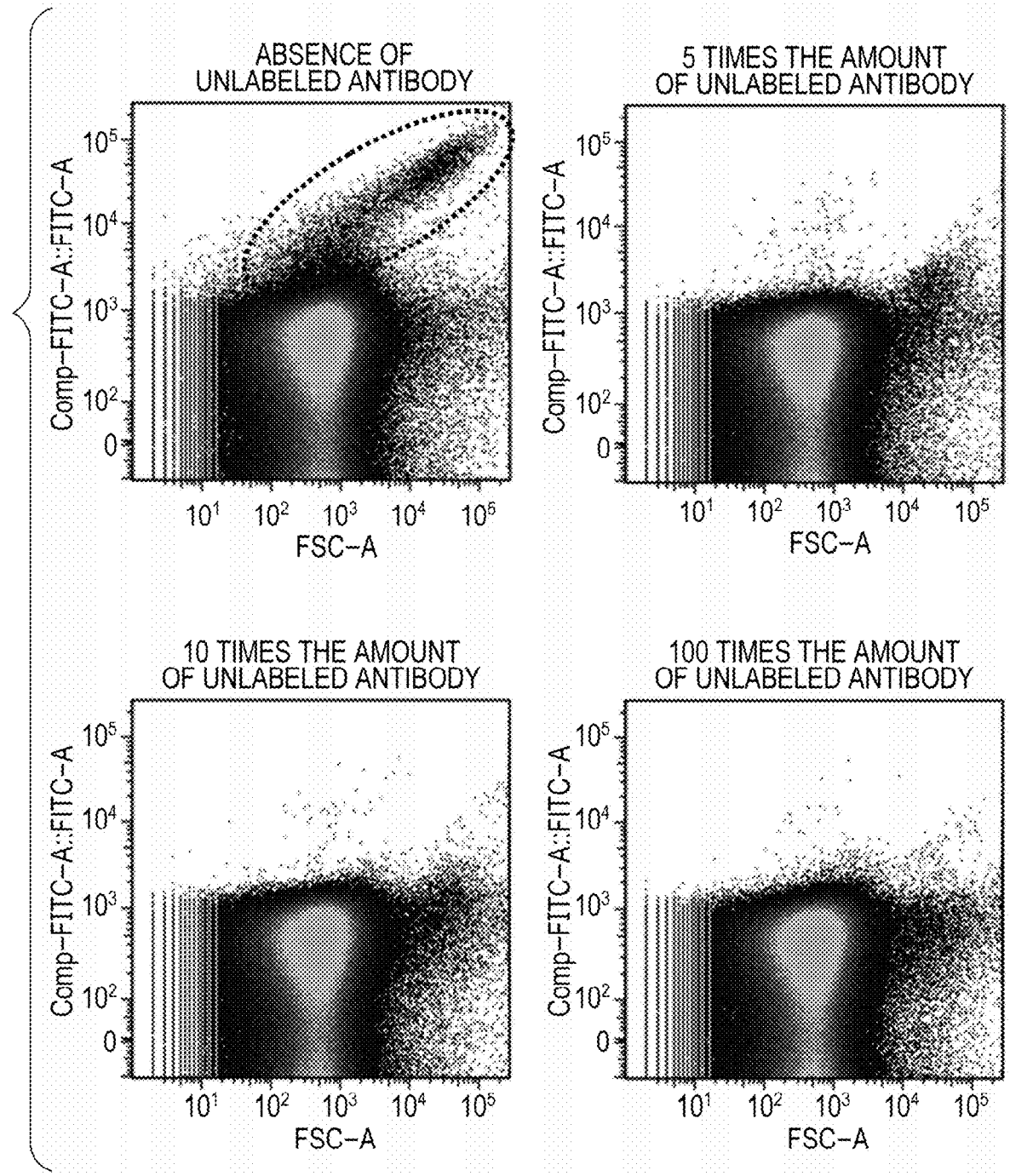
FIG. 11 illustrates results of flow cytometry of an extracellular vesicle using the anti-CD61 antibody.

FIG. 11 illustrates results of flow cytometry of the extracellular vesicle using the anti-CD61 antibody. The signals in the parts surrounded by the dotted line in the upper left diagram (without unlabeled antibody) in FIG. 11 disappeared in the upper right diagram (5 times the amount of unlabeled antibody), the lower left diagram (10 times the amount of unlabeled antibody), the lower right diagram (100 times the amount of unlabeled antibody) in FIG. 11. This indicated that the inhibitory effect could be obtained by making the unlabeled antibody and the detection antibody compete with each other.

3. Example 3

In this example, the extracellular vesicle was once immobilized on the solid phase, the detection antibody was reacted with the extracellular vesicle, then a measurement sample in which a complex of the detection antibody and the extracellular vesicle was dissociated from the solid phase was subjected to a flow cytometric analysis.

3-1. Reaction Between Extracellular Vesicle and Detection Antibody

An APC-labeled anti-CD235a antibody (clone: HIR2, BioLegend, Inc., 306608) was used as a detector. An APC-labeled Isotype control IgG2b (clone: MPC-11, BioLegend, Inc., 400320) was used as an isotype control (negative antibody control). A desthiobiotin-labeled anti-CD235a antibody (clone: HIR2, BioLegend, Inc., 306602) was used as a capturer. The reaction between the extracellular vesicle and the detection antibody was carried out in accordance with the following procedure.

i. A PBS solution of the desthiobiotin-labeled anti-CD235a antibody or the isotype control antibody was prepared so that the volume was 2 μg/ml, and streptavidin was added to a solid-phased 96-well plate at 100 μg/well, which was incubated for 1 hour.

ii. The antibody solution in the 96-well plate was discarded, the 96-well plate was washed with PBS three times, to which plasma was added at 100 μl/well, which was incubated for 1 hour to capture the extracellular vesicle in the plasma on the 96-well plate.

iii. The plasma in the 96-well plate was discarded, the 96-well plate was washed with PBS three times, and the APC-labeled anti-CD235a antibody or the isotype control antibody in a concentration of 1 μg/ml was incubated at 100 μl/well for 1 hour to form an immunoconjugate.

iv. The antibody solution in the 96-well plate was discarded, the 96-well microplate was washed with PBS three times, to which 1 mM of biotin solution was added at 100 μl/well, the biotin is brought into contact with the immunoconjugate for 1 hour to elute the immunoconjugate, the solution in the wells was collected as a measurement sample.

The flow cytometry was carried out in accordance with the conditions described in the above reference example.

3-2. Results

Figure 12A:
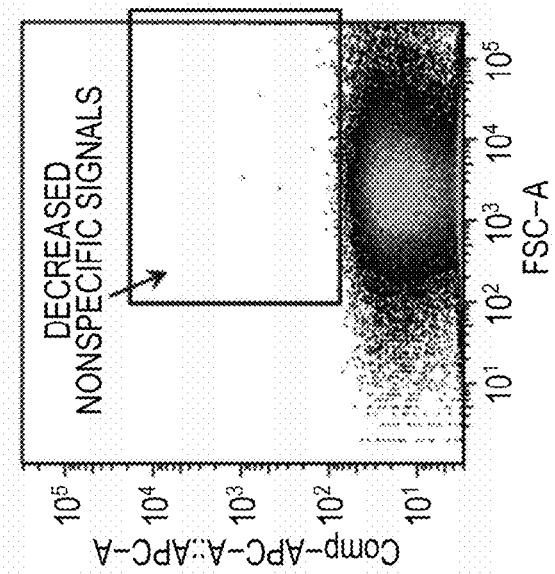
FIG. 12A illustrates signals detected using the APC-labeled anti-CD235a antibody in accordance with the method of the present disclosure.
Figure 12B:
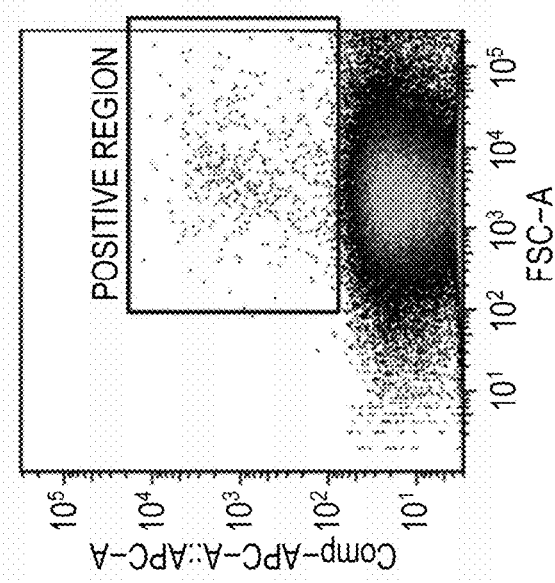
FIG. 12B illustrates signals detected using the APC-labeled isotype control antibody in accordance with the method of the present disclosure.

FIG. 12 illustrates the results obtained by the flow cytometer. FIG. 12A illustrates signals detected using the APC-labeled anti-CD235a antibody in accordance with the method of the present disclosure. FIG. 12B illustrates signals detected using an APC-labeled isotype control antibody in accordance with the method of the present disclosure. An area within a positive region frame shown in FIG. 12A is a region in which signals fundamentally attributed to the CD235a on the extracellular vesicle are detected. In FIG. 8B, nonspecific signals were detected in this region. In contrast, in FIG. 12B, nonspecific signals remarkably decreased. This indicates that the method in the present disclosure is effective for decreasing the nonspecific signals in detecting the extracellular vesicle using a flow cytometer.

What is claimed is:

1. A method for counting fluorescently-labeled bioparticles, said method comprising:
performing flow cytometry on a first measurement sample and on a second measurement sample, and counting, by said flow cytometry, the number of fluorescently-labeled bioparticles in said first and second measurement samples; and
subtracting the number of fluorescently-labeled bioparticles counted in said first measurement sample from the number of fluorescently-labeled bioparticles counted in said second measurement sample, wherein
the first measurement sample is prepared by contacting a first sample, sampled from a specimen containing a bioparticle, with a detector capable of binding to the bioparticle, wherein said detector contains a fluorescent substance, and wherein the contacting occurs in the presence of an inhibitor capable of binding to the bioparticle, and
the second measurement sample is prepared by contacting a second sample, sampled from the same specimen independently from the first sample, with the detector, wherein the contacting occurs in the substantial absence of the inhibitor,
wherein the detector binds to a target site in a protein or sugar chain molecule present in the bioparticle, wherein the inhibitor contains none of the fluorescent substance and the inhibitor is an antibody that binds to said target site to inhibit the detector from binding to said target site, and wherein the detector is at least one selected from the group consisting of an antibody and a lectin,
wherein the fluorescently labeled bioparticles are extracellular vesicles.

2. The method according to claim 1, wherein, in preparation of the first measurement sample, the first sample and the inhibitor are mixed and subsequently the detector and the mixture of the first sample and the inhibitor are mixed to prepare the first measurement sample.

3. The method according to claim 1, wherein, in preparation of the first measurement sample, the detector, the inhibitor and the first sample are mixed so that the detector and the inhibitor compete with each other in binding to the bioparticle to prepare the first measurement sample.

4. The method according to claim 1, wherein the specimen is selected from the group consisting of whole blood, plasma, serum, cerebrospinal fluid, lymph, and interstitial fluid.

5. The method according to claim 1, wherein a size of the bioparticle is 30 nm or larger and 1,000 nm or smaller.

6. The method according to claim 1, wherein the extracellular vesicles are at least one selected from the group consisting of exosomes, microparticles, and apoptotic bodies.

7. A method for counting fluorescently-labeled bioparticles, said method comprising:
counting the number of fluorescently-labeled bioparticles in a measurement sample; and subtracting non-specific counts from the number of fluorescently-labeled bioparticles counted in said measurement sample, wherein the number of fluorescently-labeled bioparticles in said measurement sample is counted by: (1) contacting a sample, sampled from a specimen containing a bioparticle, with a detector capable of binding to the bioparticle, to produce the measurement sample; and (2) counting the number of fluorescently-labeled bioparticles in the measurement sample by flow cytometry, wherein said detector contains a fluorescent substance, wherein the non-specific counts are determined by: (1) contacting the sample with the detector in the presence of an inhibitor capable of binding to the bioparticle, to produce a mixture; and (2) counting the number of fluorescently-labeled bioparticles in said mixture by flow cytometry, wherein the detector binds to a target site in a protein or sugar chain molecule present in the bioparticle, wherein the inhibitor contains none of the fluorescent substance and the inhibitor is an antibody that binds to said target site to inhibit the detector from binding to said target site, and wherein the detector is at least one selected from the group consisting of an antibody and a lectin wherein the fluorescently labeled bioparticles are extracellular vesicles.

* * * * *